US00PP26960P3

(12) United States Plant Patent
Van Swieten

(10) Patent No.: US PP26,960 P3
(45) Date of Patent: Jul. 19, 2016

(54) *PHALAENOPSIS* ORCHID PLANT NAMED 'PHALDRIBIP'

(50) Latin Name: ***Phalaenopsis* Hybrid**
Varietal Denomination: PHALDRIBIP

(71) Applicant: ANTHURA B.V., Bleiswijk (NL)

(72) Inventor: Martinus Nicolaas Gerardus Van Swieten, The Hague (NL)

(73) Assignee: ANTHURA B.V., Bleiswijk (NL)

( * ) Notice: Subject to any disclaimer, the term of this patent is extended or adjusted under 35 U.S.C. 154(b) by 81 days.

(21) Appl. No.: 14/544,164

(22) Filed: Dec. 4, 2014

(65) Prior Publication Data

US 2016/0165784 P1 Jun. 9, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Apr. 14, 2016. p. 1.*

* cited by examiner

*Primary Examiner* — Annette Para
(74) *Attorney, Agent, or Firm* — Jondle & Associates, P.C.

(57) ABSTRACT

A new and distinct variety of *Phalaenopsis* plant named 'PHALDRIBIP', particularly characterized by having purple flowers, 1 to 2 peduncles, a peduncle that is long and moderate, leaves that are oblong and moderately elongated, and is propagated by tissue culture is disclosed.

3 Drawing Sheets

Genus and species: *Phalaenopsis* Hybrid.
Variety denomination: 'PHALDRIBIP'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDRIBIP'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes or panicles, often with many showy flowers which open in succession beginning with the lowermost. The flowers possess three sepals and three petals; the lateral ones being alike. The lowermost petals, called the labellum, are three-lobed and are often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDRIBIP' is particularly characterized by its attractive and unique purple flowers, economical propagation by tissue culture, rapid growth, and a plant dimension suitable for packaging and shipping to the market.

'PHALDRIBIP' is a product of a planned breeding program conducted in Bleiswijk, The Netherlands.

The new *Phalaenopsis* 'PHALDRIBIP' originated from a cross made in February 2005 in Bleiswijk, The Netherlands. The female parent is a purple *Phalaenopsis* pot plant named '00001-0383' (unpatented), while the male parent is a purple *Phalaenopsis* pot plant named '21440-0002' (unpatented). A single plant was selected in May 2008 and has been asexually reproduced repeatedly by meristem tissue culture in Bleiswijk, The Netherlands over a 3-year period. The new variety has been found to retain its distinctive characteristics through successive asexual propagations.

Asexual reproduction of 'PHALDRIBIP' by tissue culture was first performed in December 2011 in Bleiswijk, The Netherlands and has demonstrated that the new cultivar is firmly fixed and retained through successive generations of asexual reproduction.

Plant Breeder's Rights for this variety have been applied for in Europe on Apr. 25, 2014. 'PHALDRIBIP' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Purple flowers;
2) 1 to 2 peduncles;
3) Peduncle is long and moderate;
4) The shape of the leaf is oblong and moderately elongated; and
5) Plants are propagated by meristem tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in November 2014.

DESCRIPTION OF THE NEW VARIETY

Figure 1:
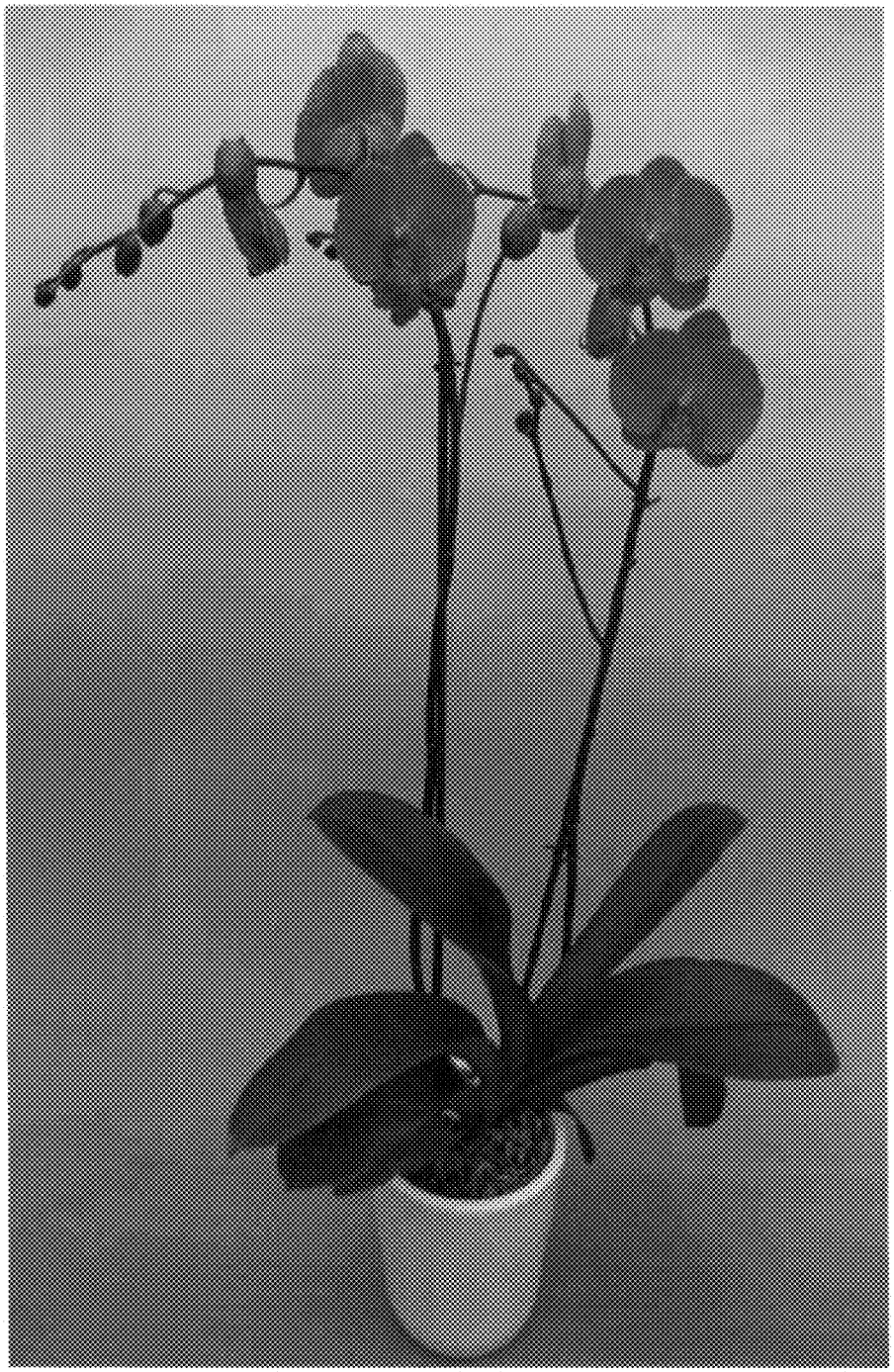
FIG. 1 shows the overall plant habit, including blooms, buds and foliage of 'PHALDRIBIP'.
Figure 2:
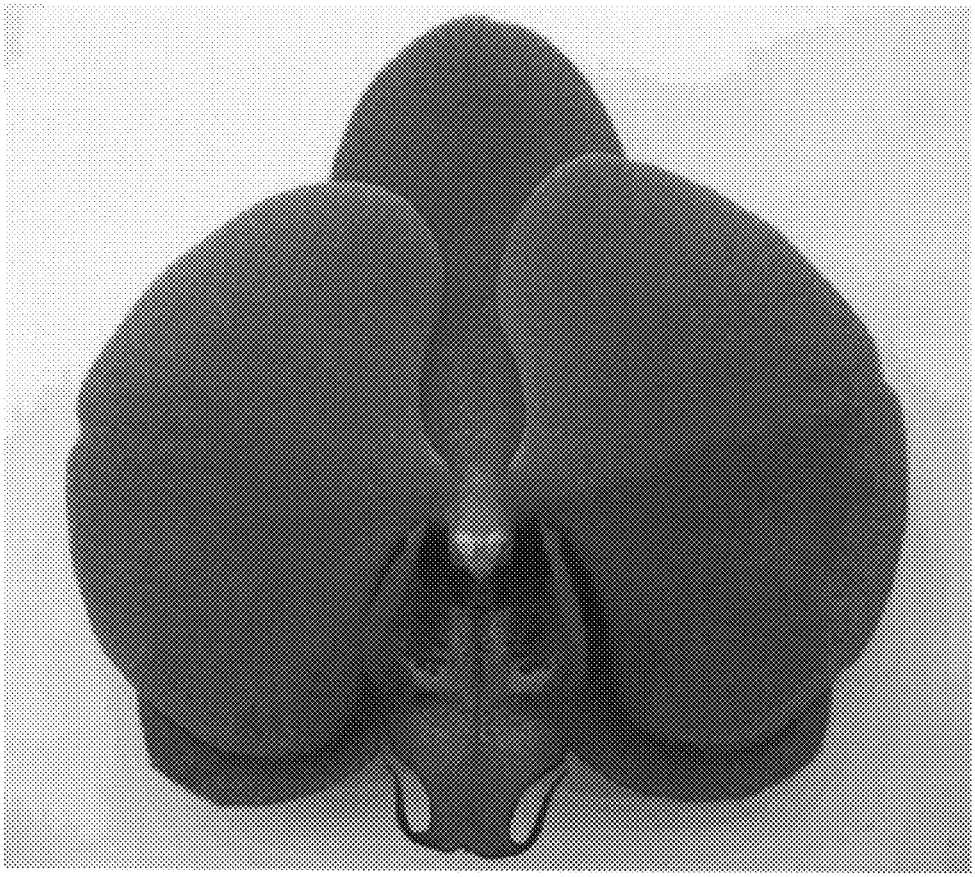
FIG. 2 shows a close-up of a flower of 'PHALDRIBIP'.
Figure 3:
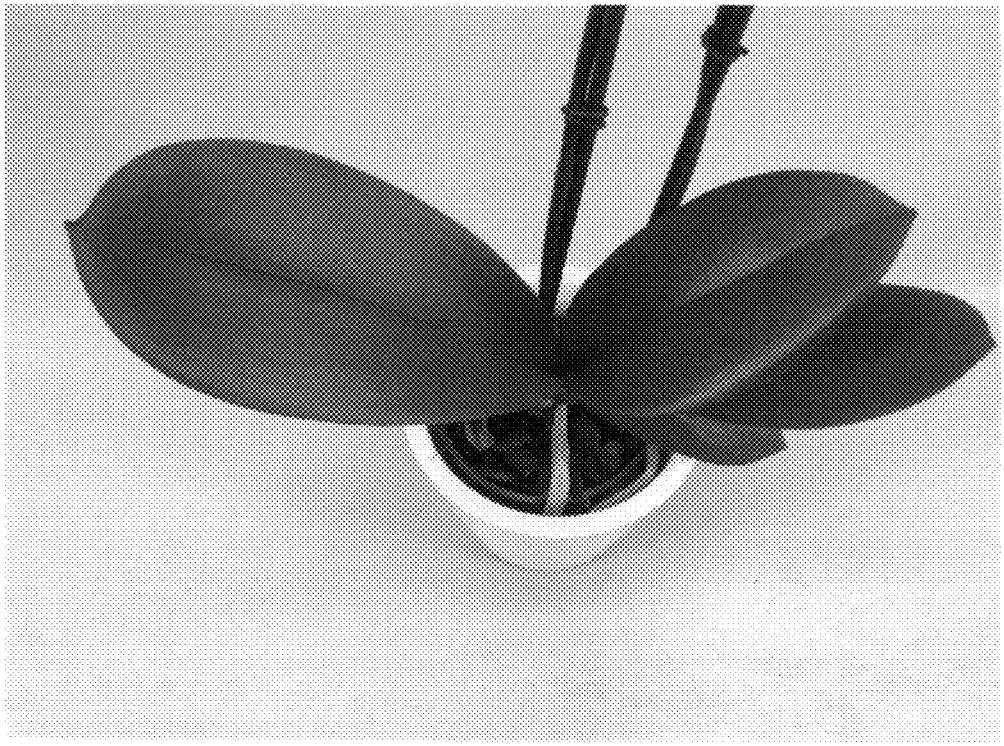
FIG. 3 shows a close-up of the leaves of 'PHALDRIBIP'.

The following detailed description sets forth the distinctive characteristics of 'PHALDRIBIP'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in November 2014. Color readings were taken under 4-6000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family*.—Orchidaceae.
- *Botanical*.—*Phalaenopsis* Hybrid.
- *Common name*.—*Phalaenopsis*.
- *Variety name*.—'PHALDRIBIP'.

Parentage:
- *Female parent*.—*Phalaenopsis* cultivar '00001-0383' (unpatented).
- *Male parent*.—*Phalaenopsis* cultivar '21440-0002' (unpatented).

Propagation:
- *Type*.—Tissue culture.

Plant:
- *Crop time* (*time to produce a finished flowering plant*).—48 to 50 weeks for a 12 cm pot.
- *Growth habit of peduncle*.—Standard, green leaves, raceme to panicle.
- *Height* (*including pot, including inflorescence*).—62.0 cm to 72.0 cm.
- *Width* (*measured from leaf tips*).—25.0 cm to 30.0 cm.
- *Vigor*.—Moderate.

Roots:
- *Root description*.—Grey-green-colored roots with lightly branching lateral roots having grey-green colored root tips.

Leaves:
- *Mature leaves*.—Quantity per plant: 5 to 6 leaves are produced before flowering. Length (fully expanded): 20.0 cm to 24.0 cm. Width: 8.0 cm to 9.0 cm. Shape: Oblong. Base shape: Moderately elongated. Apex: Unequal obtuse. Leaf blade angle with the petiole: Between 25 degrees and 35 degrees. Leaf margin: Entire. Color: Upper surface: RHS 147A. Lower surface: RHS 146A; margin of leaf is greyed-purple RHS 187A. Texture: Rough. Thickness: 2.3 mm to 2.8 mm. Venation: Pattern: Parallel. Color of the midvein: Upper surface: RHS 147A. Lower surface: RHS 187A.

Peduncle:
- *Quantity per plant*.—1 to 2.
- *Number of flowers per peduncle*.—10 to 15.
- *Length*.—68.0 cm to 73.0 cm.
- *Diameter*.—5.3 mm to 5.8 mm.
- *Strength*.—Moderate.
- *Aspect*.—Upright.
- *Texture*.—Smooth.
- *Color*.—Brown (RHS 200A).
- *Internode length*.—40.0 mm to 50.0 mm.
- *Callosities*.—None.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base to tip): 220.0 mm to 270.0 mm. Diameter: 4.1 mm to 4.6 mm.
- *Flowering time*.—First flowers can be expected 10 to 11 months after planting in a 12 cm pot.
- *Flower*.—Height: 83.0 mm to 88.0 mm. Diameter: 98.0 mm to 103.0 mm. Depth of lip: 18.0 mm to 20.0 mm.
- *Flower longevity*.—On the plant: 10 to 13 weeks.
- *Fragrance*.—Absent.
- *Petals*.—Arrangement: Free. Shape: Semi-circular. Apex: Emarginate and slightly asymmetric. Margin: Entire. Length (from base to tip): 46.0 mm to 48.0 mm. Width: 59.0 mm to 61.0 mm. Color (when fully opened): Main color: Purple (RHS 78A). At the base: Purple (RHS 78A).
- *Dorsal sepal*.—Shape: Elliptic broad. Margin: Entire. Length (from base to tip): 48.0 mm to 50.0 mm. Width: 38.0 mm to 40.0 mm. Color (when fully opened): Main color: Purple (RHS 78A). At the base: Purple (RHS 78A).
- *Lateral sepals*.—Shape: Ovate broad. Margin: Entire. Length (from base to tip): 48.0 mm to 50.0 mm. Width: 36.0 mm to 38.0 mm. Color (when fully opened): Main color: Purple (RHS 78A), slightly dotted towards the center. At the base: Purple (RHS 78A), slightly dotted towards the center.
- *Labellum* (*lip*).—Margin: Entire. Length: 19.0 mm to 21.0 mm. Width: 20.0 mm to 22.0 mm. Whiskers: Present. Length of whiskers: Medium; 11.0 mm.
- *Lateral lobe*.—Shape: Type V (as described in the International Union for the Protection of New Varieties of Plants (UPOV) Test Guidelines for *Phalaenopsis*). Color: Red-purple (RHS 59A and 61A and 71A).
- *Apical lobe*.—Shape: Triangular. Color: Red-purple (RHS 71A), yellow towards the callus.
- *Callus*.—Color: Yellow (RHS 13A) dotted with RHS 59A.

*Pedicel*.—Length: 33.0 mm to 35.0 mm. Diameter: 3.0 mm to 3.2 mm.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 10.0 mm to 12.0 mm. Diameter: 6.5 mm to 6.9 mm. Color: Purple (RHS 78A).

*Pollinia*.—Quantity: 2. Size: 1.1 mm to 1.3 mm. Color: Orange (RHS 26A).

*Ovary*.—Length: 12.0 mm to 14.0 mm. Diameter: 2.6 mm to 2.8 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDRIBIP' differs from female parent '00001-0383' (unpatented) in that 'PHALDRIBIP' has a red-purple lip and red-purple whiskers of the lip, whereas '00001-0383' has a lip that is lighter colored (white/lilac/yellow/greyed-purple) and light purple whiskers of the lip. Additionally, 'PHALDRIBIP' has an unequal obtuse leaf apex, whereas '00001-0383' has an unequal acute leaf apex.

'PHALDRIBIP' differs from male parent '21440-0002' (unpatented) in that 'PHALDRIBIP' has a larger flower and a brown peduncle, whereas '21440-0002' has a smaller flower and a green-brown peduncle. Additionally, 'PHALDRIBIP' has leaves with a greyed-purple margin, whereas '21440-0002' does not have leaves with a greyed-purple margin.

'PHALDRIBIP' differs from commercial variety 'PHALBATZOM' (unpatented) in that 'PHALDRIBIP' has larger flowers with petals that are free, whereas 'PHALBATZOM' has smaller flowers with petals that are touching. Additionally, 'PHALDRIBIP' has a greyed-purple leaf margin, whereas 'PHALBATZOM' has a green leaf margin.

I claim:

1. A new and distinct variety of *Phalaenopsis* plant named 'PHALDRIBIP', substantially as described and illustrated herein.

* * * * *